(12) United States Patent
Bruning et al.

(10) Patent No.: US 7,704,533 B2
(45) Date of Patent: Apr. 27, 2010

(54) **COMPOSITIONS AND METHODS OF INDUCING HAIR GROWTH UTILIZING *CONTINUS COGGYGRIA***

(75) Inventors: Elizabeth Bruning, Somerset, NJ (US); Violetta Iotsova Stone, Robbinsville, NJ (US); Renbin Zhao, Plainsboro, NJ (US)

(73) Assignee: J&J Consumer Companies, Inc., Skillman, NJ (US)

( * ) Notice: Subject to any disclaimer, the term of this patent is extended or adjusted under 35 U.S.C. 154(b) by 0 days.

(21) Appl. No.: 11/952,399

(22) Filed: Dec. 7, 2007

(65) Prior Publication Data

US 2008/0145331 A1  Jun. 19, 2008

Related U.S. Application Data

(60) Provisional application No. 60/869,770, filed on Dec. 13, 2006.

(51) Int. Cl.
*A01N 65/00* (2009.01)
(52) U.S. Cl. ........................ 424/725; 514/880
(58) Field of Classification Search ........................ None
See application file for complete search history.

(56) References Cited

U.S. PATENT DOCUMENTS

| | | |
|---|---|---|
| 5,216,116 A | 6/1993 | Pawelek |
| 5,218,079 A | 6/1993 | Pawelek et al. |
| 5,225,435 A | 7/1993 | Pawelek et al. |
| 5,227,459 A | 7/1993 | Pawelek et al. |
| 5,384,116 A | 1/1995 | Pawelek et al. |
| 5,618,519 A | 4/1997 | Pawelek et al. |
| 5,744,125 A | 4/1998 | Pawelek et al. |
| 7,025,951 B2 | 4/2006 | Seiberg et al. |
| 7,049,331 B2 | 5/2006 | Eisinger et al. |
| 2006/0088608 A1* | 4/2006 | Seiberg et al. ............... 424/725 |

FOREIGN PATENT DOCUMENTS

RU  2014784 C1 *  6/1994
WO  WO 2006/057755 A2  1/2006

OTHER PUBLICATIONS

Kultur et al., "Medicinal Plants Used in Kirklareli Province (Turkey)", Journal of Ethnopharmacology, Elsevier Scientific Publishers Ltd., IE, vol. 111, No. 2, Dec. 12, 2006, pp. 341-364.
Otberg et al., "Androgenetic Alopecia", Endocrinology and Metabolism Clinics of North America, vol. 36, No. 2, 2007, pp. 379-398.
Price, V.H., "Andorgenetic Alopecia in Women", The Society of Investigative Dermatology, Inc. vol. 8, No. 1, 2003, pp. 24-27.
Pickard-Holley, S., "The Symptom Experience of Alopecia", Seminars in Oncology Nursing, vol. 11, No. 4, Nov., 1995, pp. 235-238.
Imperato-McGinley et al., "Steroid 5α-Reductase Deficiency in Man: An Inherited Form of Male Pseudohermaphroditism", Department of Medicine, Division of Endocrinology, vol. 186, 1974, pp. 1213-1215.
Price et al., "Lack of Efficacy of Finasteride in Postmenopausal Women with Androgenetic Alopecia", Journal of American Academy of Dermatology, Nov. 2000, pp. 768-776.
http://www.folca.com/Hair Loss Treat d1283.html, Aug. 27, 2009.
http://www.bpg.bg/alenmak/natural.phtml, Aug. 27, 2009.
http://www.herbnet.com/Herb%20Uses RST.htm, Aug. 27, 2009.
International Cosmetic Ingredient Dictionary and Handbook, eds. Wenninger and McEwen, pp. 1656-1661, 1626, and 1654-1655. (The Cosmetic, toiletry, and Fragrance Association, Washington, DC 7th Edition, 1997).
Takahashi et al., "Procyanidin Oligomers Selectively and Intensively Promote Proliferation of Mouse Hair Epithelial Cells In Vitro and Activate Hair Follicle Growth In Vivo", The Journal of Investigative Dermatology, Inc., vol. 112, 1999.
International Search Report dated May 8, 2009, for corresponding international application PCT/US2007/087070.

* cited by examiner

*Primary Examiner*—Michele Flood
*Assistant Examiner*—Qiuwen Mi

(57) ABSTRACT

Compositions and methods for inducing hair growth and improving hair quality utilizing extracts of *Cotinus coggygria* in an amount effective to induce hair growth when applied topically to an area of the skin on which hair growth is desired.

2 Claims, No Drawings

COMPOSITIONS AND METHODS OF INDUCING HAIR GROWTH UTILIZING *CONTINUS COGGYGRIA*

This application is a non-provisional patent application claiming priority of U.S. Provisional Patent Application Ser. No. 60/869,770, filed Dec. 13, 2006 and incorporates the subject matter thereof by reference.

FIELD OF THE INVENTION

This invention relates to topical compositions and methods of inducing hair growth and improving hair quality utilizing extracts from the plant *Cotinus coggygria*.

BACKGROUND OF THE INVENTION

Genetic disposition as well as the natural aging process and/or disease contribute to hair loss and slower hair growth in both males and females. Approximately 50% of the population displays this trait to some degree by the age of 50, where thinning of the hair can begin between 12 and 40 years of age independent of gender (Otberg N et al. Androgenetic alopecia. *Endocrinol Metab Clin North Am.* 2007; 36(2)379-398 and Price V H. Androgenetic alopecia in women. *Investig Dermatol Symp Proc.* 2003; 8 (1): 24-27). Thus, agents able to stimulate hair growth as well as prevent and slow down or reduce hair loss could be beneficial not only as a cure for alopecia but also as positively affect the psychosocial events associated with hair disorders. Studies reveal psychosocial impact with hair loss to include body image dissatisfaction associated with negative stereotypes such as feeling older, weaker and less attractive (S. Pickard-Holley, The symptom experience of alopecia. *Sem. Oncol. Nurs.* 1995; 11:235-238).

Drugs, including Minoxidil (Rogaine), Finasteride (Propecia) and Dutasteride (Avodart) are approved treatments for hair loss. However, they require medical prescription, and are active only on a certain percent of the population. Moreover, some of these drugs are not permitted to be used by females because of hormonal effects. Premenopausal women should not take Finesteride due to the risk of male pseudo-hermaphroditism to the fetus (Science 1974; 186:1213-5; US package insert for Propecia® (finasteride 1 mg tablets)). In addition, a one-year, double-blind, placebo-controlled, randomized, multicenter trial has shown that Finasteride did not improve scalp hair growth in postmenopausal women (Price et al. Lack of efficacy of finasteride in postmenopausal women with androgenetic alopecia, J Am Acad Dermatol, November 2000:768-776). Finasteride was found recently to lower artificially the results of the prostate-specific antigen (PSA) test, the standard screening test for prostate cancer which can delay the detection and the treatment of the disease (http://healthorbit.ca/NewsDetail.asp?opt=1&nltid=037041206).

Minoxidil is a drug that is effective in inducing hair growth for a small percentage of patients and will re-grow hair only on top of the scalp. Further, it has limited effect on older people. Minoxidil may slow the rate of hair loss in five out of ten male patients.

Other medical treatments available to treat hair loss include drastic surgical techniques such as scalp reduction, scalp flaps or follicular unit transplantation. These surgeries carry the risk of complications such as elevation of hairline associated with donor region, possibility of necrosis and unnatural appearance of hair growth direction, anesthesia and post-op care, not to mention high costs.

Herbal preparations that claim to induce hair growth (e.g. Hair Prime) are available at low cost but their effectiveness is very limited.

*Cotinus coggygria* has been suggested for use in anti-inflammatory, wound healing, antiseptic and astringent applications. See also copending U.S. patent application Ser. Nos. 10/973,313, 11/248,465, 11/313,079, 11/387,892 and Ser. No. 11/590,563 filed Oct. 31, 2006.

This extract is also used as a cholagogue, febrifuge and for eye ailments. Recent research shows that *Cotinus coggygria* syrup has the effect of protecting the liver from chemical damage, reducing tension of the choledochal sphincter, increasing bile flow and raising the body immunity. The anti-hepatitis effect of *Cotinus coggygria* may be carried out through the mechanisms of decreasing transaminase, normalizing functioning of the gallbladder, reducing icterus and 10 enhancing the immunity of the body.

Surprisingly, we have found that a concentrated, aqueous *Cotinus coggygria* extract can effectively induce hair growth when topically applied. We observed a potent increase in hair growth in vivo in all animals treated with a concentrated *Cotinus coggygria* extract. More surprisingly, the Cotinus extract induced hair growth faster than 5% Minoxidil.

SUMMARY OF THE INVENTION

As used herein, "topical application" means directly laying on or spreading on outer skin using, e.g., by use of the hands or an applicator such as a wipe, puff, roller, or spray.

As used herein, "cosmetically-acceptable" means that the product(s) or compound(s) which the term describes are suitable for use in contact with tissues (e.g., the skin) without undue toxicity, incompatibility, instability, irritation, allergic response, and the like. This term is not intended to limit the ingredient/product, which it describes to use solely as a cosmetic (e.g., the ingredient/product may be used as a pharmaceutical).

As used herein, "topical carrier" means one or more compatible solid or liquid filler diluents that are suitable for topical administration to a mammal. Examples of topical carriers include, but are not limited to, water, waxes, oils, emollients, emulsifiers, thickening agents, gelling agents, and mixtures thereof.

As used herein, "hair" means scalp, head, facial and/or body hair, including but not limited to the scalp, eye lashes, brows, mustache, beard, ear, nasal, chest, pubic, auxiliary and the like.

As used herein, "inducing hair growth" means the earlier induction of growth of a new hair cycle, and/or prolonging the active growth phase (anagen) of the hair cycle and/or increasing the growth rate of the hair and/or increasing the width of hair shaft, including, but not limited to, the induction of the growth of hair and making it more visible to the eye.

As used herein, "improving hair quality" means increasing the diameter of the hair shaft and/or enhancing the visual attributes of the hair like hair volume, hair shine and hair thickness, and/or affecting the characteristics of the hair shaft and/or hair cuticles, including, but not limited to, creating a smoother look or feel, and/or increase in shine.

As used herein, "safe and effective amount" means an amount of a physiologically active compound or composition sufficient to induce a positive modification in the condition to be regulated or treated, (e.g. hair growth) but low enough to avoid serious side effects. The safe and effective amount of the compound or composition will vary with the particular condition being treated, the age and physical condition of the end user, the severity of the condition being treated/prevented, the duration of the treatment, the nature of other treatments, the specific compound or product/composition employed, the particular cosmetically-acceptable carrier utilized, and like factors.

We have found that a *Cotinus coggygria* extract having a concentration from about 60 to about 210 mg/ml and most preferably at about 150 mg/ml of solids, when applied regularly to an area on a mammal in which hair growth is desired, induces the growth of hair in that area. An amount of 60 mg/ml was able to induce hair growth compared to placebo and untreated, and the effect significantly increased with the more concentrated 150 mg/ml dose.

Such *Cotinus coggygria* extract may be applied topically to an area on which a subject desires to induce hair growth in a safe and effective amount as part of a cosmetically acceptable composition over a period of time and in an amount sufficient to induce hair growth.

DETAILED DESCRIPTION OF PREFERRED EMBODIMENTS

Plant Extract

In one embodiment, the compositions of present invention contain an aqueous extract of *Cotinus coggygria* leaves. What is meant by "an aqueous extract of *Cotinus coggygria* leaves" is a blend of compounds isolated from the leaves by physically removing the leaves of such plant, such as by grinding of the plant, and subjecting them to an aqueous extraction process, such as that described hereinbelow.

In one embodiment, the *Cotinus coggygria* extract is present in the composition in an amount from about 0.001% to about 30% by weight, in particular in an amount from about 0.1% to about 25% and most preferably at 5-20% by weight of the composition. Unless stated otherwise, the weight of the extract refers to the dry weight of the extract.

More particularly, the *Cotinus coggygria* plant extracts useful in the compositions and methods of this invention are preferably prepared as follows so as to concentrate and purify the active moieties of the *Cotinus coggygria* plant. *Cotinus coggygria* leaves (whole dried leaves including sticks) may be obtained from Bulgaria, Poland or China, although *Cotinus coggygria* may be cultivated elsewhere in the world. The leaves may then be crushed and the larger sticks removed to facilitate extraction. The remaining material should be placed in boiling water and boiled for at least about two minutes and up to about thirty minutes in a sealed container with agitation as needed. Longer boiling time is acceptable but will not extract a substantial amount of material. After the boiling process is complete, the container should be immediately withdrawn from the heating source, kept covered, and stored at room temperature for from about 1 hour to about 12 hours. This may be accompanied with occasional agitation; the longer the mixture is stored, the less agitation may be needed. The extract should then be filtered, and excess liquid removed from the material. The resulting extract constitutes a concentration of approximately 30 mg/ml *Cotinus coggygria* extract. In order to prepare more concentrated material, the extract should be further concentrated by reducing the volume to between about two and about five times its original yield to produce between a 60 mg/ml and a 150 mg/ml extract. This process should be achieved by heating and evaporating the material on a stirrer plate at a most preferred temperature of between about 80° C. and about 85° C. The extract may then be stored at 4° C. without losing activity.

Alternatively, the *Cotinus coggygria* extract of this invention may be concentrated by the process of lyophilization. A 30 mg/ml *Cotinus coggygria* extract may be prepared as described earlier and concentrated via a lyophilization technique in, for example, a Genesis freeze dryer (commercially available from VIRTIS, Gardiner, N.Y.) as follows: a standard freeze drying cycle should include subjecting the material to a freezing temperature of at least about $-70$ C.° and drying vacuum of 20 mmHg. This cycle maybe repeated to remove all the water from the extract. Increasingly concentrated material may be made by weighing the container before and after lyophilization, and adding deionized water to dissolve the solids into the desired concentration of *Cotinus*. The resulting extracts may then be frozen at a temperature of about $-20$ C.° or an appropriately low temperature for long term storage. Such extracts obtained via lyophilization are effective in inducing hair growth.

Other ways of making concentrated *Cotinus* extract may include spray drying the 30 mg/ml extract and dissolving the resultant powder in deionized water, or in organic solvent (e.g. ethanol, or in water/organic solvent mixtures) to appropriate concentration. We believe that such extracts obtained via lyophilization should be effective in inducing hair growth.

Topical Compositions

The topical compositions useful in this invention contain formulations suitable for topical application to skin. In one embodiment, the composition contains a concentrated *Cotinus coggygria* extract and a cosmetically-acceptable topical carrier. In one embodiment, the cosmetically-acceptable topical carrier constitutes from about 50% to about 99.99%, by weight, of the composition more preferably from about 80% to about 95%, by weight, of the composition.

The compositions of this invention may be made into a wide variety of product types that include but are not limited to solid and liquid compositions such as lotions, creams, gels, sticks, sprays, ointments, cleansing liquid washes and solid bars, shampoos, pastes, powders, foams, mousses, and wipes. These product types may contain several types of cosmetically acceptable topical carriers including, but not limited to solutions, emulsions (e.g., microemulsions and nanoemulsions), gels, solids and liposomes. The following are non-limiting examples of such carriers. Other carriers can be formulated by those of ordinary skill in the art.

The topical compositions useful in the present invention can be formulated as solutions. Solutions should preferably include an aqueous solvent (e.g., from about 50% to about 99.99% or from about 90% to about 99% of a cosmetically acceptable aqueous solvent). More preferably, such compositions should contain about 30% solvent, although this may vary dependent upon the formulation. Such solvents may include ethanol, propylene glycol, polyethylene glycol, mixtures thereof and the like which are good carriers for successful delivery to the hair follicles.

Topical compositions useful in the subject invention may be formulated as a solution containing an emollient. Such compositions preferably contain from about 2% to about 50% of an emollient(s). As used herein, "emollients" refer to materials used for the prevention or relief of dryness, as well as for the protection of the skin. A wide variety of suitable emollients are known and may be used herein. The International Cosmetic Ingredient Dictionary and Handbook, eds. Wenninger and McEwen, pp. 1656-61, 1626, and 1654-55 (The Cosmetic, Toiletry, and Fragrance Assoc., Washington, D.C., 7$^{th}$ Edition, 1997) (hereinafter "INCI Handbook") contains numerous examples of suitable materials.

A lotion may be made from a solution. Lotions typically contain from about 1% to about 20% (more preferably, from about 5% to about 10%) of an emollient(s) and from about 50% to about 90% (more preferably, from about 60% to about 80%) of water.

Another type of product may be a solution that is a cream. A cream typically comprises from about 5% to about 50% (more preferably, from about 10% to about 20%) of an emollient(s) and from about 45% to about 85% (more preferably, from about 50% to about 75%) of water.

Yet another type of product that may be formulated from a solution is an ointment. An ointment may be constituted of a simple base of animal or vegetable oils or semi-solid hydrocarbons. An ointment may contain from about 2% to about 100% of an emollient(s), and from about 0.1% to about 2% of a thickening agent(s). The INCI Handbook contains a list of acceptable thickening agents or viscosity increasing agents useful in the compositions and methods of this invention at pages 1693 through 1697.

The topical compositions useful in the present invention may also be preferably formulated as emulsions. If the carrier is an emulsion, from about 1% to about 10% (preferably from about 2% to about 5%) of the carrier should be made up one or more emulsifiers. Emulsifiers may be nonionic, anionic or cationic. Suitable emulsifiers may be found in, for example, the INCI Handbook, pp. 1673-1686.

Lotions and creams may also be formulated as emulsions. Typically such lotions preferably contain from 0.5% to about 5% of an emulsifier(s). Such creams would typically comprise from about 1% to about 20% (preferably from about 5% to about 10%) of an emollient(s); from about 20% to about 80% (preferably, from 30% to about 70%) of water; and from about 1% to about 10% (preferably, from about 2% to about 5%) of an emulsifier(s).

Single emulsion skin care preparations, such as lotions and creams, of the oil-in-water type and water-in-oil type are well-known in the cosmetic art and are useful in the subject invention. Multiphase emulsion compositions, such as the water-in-oil-in-water type are also useful in the subject invention. In general, such single or multiphase emulsions contain water, emollients, and emulsifiers as essential ingredients.

Compositions of this invention may also be in the form of shampoo, hair conditioning products, leave-on hair masks, mousse, sprays, in combination with dyes and other hair care products for cleaning, treating, conditioning and coloring the hair simultaneous with topical application of the novel compositions of this invention.

The topical compositions of this invention may be formulated as a gel (e.g., an aqueous gel using a suitable gelling agent(s)). Suitable gelling agents for aqueous gels include, but are not limited to, natural gums, acrylic acid and acrylate polymers and copolymers, and cellulose derivatives (e.g., hydroxymethyl cellulose and hydroxypropyl cellulose). Suitable gelling agents for oils (such as mineral oil) include, but are not limited to, hydrogenated butylene/ethylene/styrene copolymer and hydrogenated ethylene/propylene/styrene copolymer. Such gels typically comprises between about 0.1% and 5%, by weight, of such gelling agents. Microgels may be used to enhance follicular delivery of the formulations.

The topical compositions of this invention may also be formulated into a solid formulation (e.g., a wax-based stick, mascara, soap bar composition, powder, or a wipe containing powder.

The topical compositions useful in this invention may contain, in addition to the aforementioned components, a wide variety of additional oil-soluble, organic solvent-soluble, and/or water-soluble materials conventionally used in compositions for use on skin and hair, at their art-established levels. For example, a formulation of 70% ethanol and 30% propylene glycol or variable amounts of these two agents may be used for enhanced delivery of the actives.

Surfactants

In one embodiment, the composition of this invention contains one or more surfactants. In one embodiment, the composition contains a lathering surfactant. What is meant by a "lathering surfactant" is a surfactant that generates lather when combined with water and mechanically agitated. In one embodiment, the lathering surfactant has an initial foam height reading of at least 20 mm, such as at least 50 mm, in the Standard Test Method for Foaming Properties of Surface-Active Agents D1173-53 Set forth in the ASTM Annual Book of ASTM Standards 1001 Section 15 Volume 15.04 (using a concentration of 5 grams per liter, temperature of 49° C., and water hardness of 8 grains per gallon). Examples of lathering surfactants include, but are not limited to, anionic, nonionic, cationic, and amphoteric lathering surfactants.

Nonlimiting examples of anionic lathering surfactants include those selected from the group consisting of sarcosinates, sulfates, isethionates, taurates, phosphates, lactylates, and glutamates. Specific examples include, but are not limited to, those selected from the group consisting of sodium lauryl sulfate, ammonium lauryl sulfate, ammonium laureth sulfate, sodium laureth sulfate, sodium trideceth sulfate, ammonium cetyl sulfate, sodium cetyl sulfate, ammonium cocoyl isethionate, sodium lauroyl isethionate, sodium lauroyl lactylate, triethanolamine lauroyl lactylate, sodium caproyl lactylate, sodium lauroyl sarcosinate, sodium myristoyl sarcosinate, sodium cocoyl sarcosinate, sodium lauroyl methyl taurate, sodium cocoyl methyl taurate, sodium lauroyl glutamate, sodium myristoyl glutamate, and sodium cocoyl glutamate and mixtures thereof.

Nonlimiting examples of nonionic lathering surfactants include those selected from the group consisting of alkyl glucosides, alkyl polyglucosides, polyhydroxy fatty acid amides, alkoxylated fatty acid esters, lathering sucrose esters, amine oxides, and mixtures thereof. Specific examples include, but are not limited to, nonionic surfactants to those selected form the group consisting of C8-C14 glucose amides, C8-C14 alkyl polyglucosides, sucrose cocoate, sucrose laurate, lauramine oxide, cocoamine oxide, and mixtures thereof.

Nonlimiting examples of amphoteric lathering surfactants (which also includes zwitterionic lathering surfactants are those selected from the group consisting of betaines, sultaines, hydroxysultaines, alkyliminoacetates, iminodialkanoates, aminoalkanoates, and mixtures thereof.

Nonlimiting examples of amphoteric surfactants of the present invention include disodium lauroamphodiacetate, sodium lauroamphoacetate, cetyl dimethyl betaine, cocoamidopropyl betaine, cocoamidopropyl hydroxy sultaine, and mixtures thereof.

Additional Cosmetically Active Agents

In one embodiment, the compositions according to this invention may further contain one or more additional cosmetically active agent(s) as well as the above-mentioned components. What is meant by a "cosmetically active agent" is a compound, which may be a synthetic compound or a compound isolated, purified or concentrated from a natural source, or a natural extract containing a mixture of compounds, that has a cosmetic or therapeutic effect on the tissue, including, but not limited to: anti-microbial agents such as anti-yeast agents, anti-fungal, and anti-bacterial agents, anti-inflammatory agents, anti-aging agents, anti-parasite agents, external analgesics, sunscreens, photoprotectors, antioxidants, keratolytic agents, detergents/surfactants, moisturizers, nutrients, vitamins, minerals, energy enhancers, antiperspiration agents, astringents, hair growth enhancing agents, hair coloring agents, pigments, firming agents, agents for skin conditioning, and odor-control agents such as odor masking or pH-changing agents.

In one embodiment, the cosmetically active agent may be selected from, but not limited to, the group consisting of hydroxy acids, benzoyl peroxide, D-panthenol, octyl methoxycinnimate, titanium dioxide, octyl salicylate, homosalate, avobenzone, carotenoids, free radical scavengers, spin traps, retinoids such as retinoic acid (tretinoin) and retinoid precursors such as retinol and retinyl palmitate, vitamins such as vitamin E (alpha, beta or delta tocopherols and/or their mixtures) ceramides, polyunsaturated fatty acids, essential fatty acids, enzymes, enzyme inhibitors, minerals, hormones such as progesterones, steroids such as hydrocortisone, 2-dimethylaminoethanol, metal (including but not limited to iron or zinc) salts such as copper chloride, peptides containing copper such as Cu:Gly-His-Lys, coenzyme Q10, amino acids, vitamins, acetyl-coenzyme A, niacin, riboflavin, thiamin, ribose, electron transporters such as NADH and FADH2, botanical extracts such as aloe vera, Feverfew, and Soy, and derivatives and mixtures thereof. The cosmetically active agent will preferably be present in the composition of the invention in an amount of from about 0.001% to about 20% by weight of the composition, more preferably, from about 0.005% to about 10% and most preferably, from about 0.01% to about 5%.

Also expected to be particularly effective in the compositions and methods of this invention are the presence of synthetic or natural 5-alpha reductase inhibitors, or other anti-sebum ingredients including, but not limited to, Sepicontrol (Capryloyl Glycine, Sarcosine and Cinamomum Zeylanicum Bark Extract), licorice powder or extract, and the like. MC5 receptor antagonists may also be utilized in the compositions of this invention. Examples of MC5-R antagonists may be found in U.S. Pat. No. 7,049,331.

The compositions of this invention may also be utilized in combination with compounds known to promote hair growth that are available as drugs, such as finasteride (Propecia), a type 2 5-alpha-reductase inhibitor, and dutasteride, a type 1- and 2-5-alpha-reductase inhibitor, as well as flutamide, bicalutamide, pregnane derivatives, progesterone derivatives, experimental agents such as FCE 28260 and the like. Spironolactone and other diuretics may also be utilized as it is indicated for women in some cases (also known as Aldactone: an aldosterone receptor antagonist). Potassium channel openers, such as Minoxidil (Rogaine), which are known to promote hair growth, are also believed to be especially promising combinations.

Herbal remedies_that may have 5-alpha reductase inhibitory action may include: Saw Palmetto and Pygeum africanum. Other agents that may have such activity are Beta-sisterol, Sepicontrol and Licorice, gamma-linolenic acid and other unsaturated fatty acids (Tehming LIANG and Shutsung LIAO) Biochem. J. (1992) 285, 557-562, Inhibition of steroid 5-alpha-reductase by specific aliphatic unsaturated fatty acids), Zinc and Zinc salts, green tea catechin (–)-epigallocatechin gallate (EGCG) and other polyphenols, and the like. Grape seed, apple seed, apple juice and barley extracts may also be potential agents that may induce hair growth, although they are not thought to be very common(s) or satisfactory in achieving satisfactory results (Takahashi et al., Procyanidin Oligomers Selectively and Intensively Promote Proliferation of Mouse Hair Epithelial Cells In Vitro and Activate Hair Follicle Growth In Vivo, J Invest Dermatol 112:310-316).

Additional combinations may include other known stimulators of hair growth, such as, zinc, calcineurin inhibitors such as FK506 (Tacrolimus, Fujimycin), a macrolide antibiotic produced by *Streptomyces tsukubaensis*, and its derivatives, or Cyclosporin A, a cyclic endecapeptide and a T cell-specific immunosuppressant, and the like.

Active ingredients in Provillus, a product suggested to block DHT (Vitamin B6, Biotin, Magnesium, Zinc, Saw Palmetto, Nettle, Gotu Kola, Pumpkin, Eleuthero Root, Uva-Ursi, Muria Puama) may also be included in the compositions of this invention.

Examples of vitamins that may be constituents of the compositions of this invention include, but are not limited to, vitamin A, vitamin Bs such as vitamin B3, vitamin B5, and vitamin B12, vitamin C, vitamin K, vitamin E such as alpha, gamma or delta-tocopherol, and derivatives (such as salts and esters) and mixtures thereof.

Examples of hydroxy acids include, but are not limited, to glycolic acid, lactic acid, malic acid, salicylic acid, citric acid, and tartaric acid. Such hydroxy acids, it is believed, serve to support the regeneration of the corneous layer of the scalp. We also believe that such hydroxy acids assist in normalizing the pH of the compositions of this invention and may, as with lactic acid, add a conditioning effect to the hair.

Examples of antioxidants which may be utilized in the compositions and methods of this invention include, but are not limited to, water-soluble antioxidants such as sulfhydryl compounds and their derivatives (e.g., sodium metabisulfite and N-acetyl-cysteine), lipoic acid and dihydrolipoic acid, resveratrol, lactoferrin, and ascorbic acid and ascorbic acid derivatives (e.g., ascorbyl palmitate and ascorbyl polypeptide). Oil-soluble antioxidants suitable for use in the compositions of this invention include, but are not limited to, butylated hydroxytoluene, retinoids (e.g., retinol and retinyl palmitate), different types of tocopherols (e.g., alpha-, gamma-, and delta-tocopherols and their esters such as acetate) and their mixtures, tocotrienols, and ubiquinone. Natural extracts containing antioxidants suitable for use in the compositions of this invention, include, but not limited to, extracts containing flavonoids, isoflavonoids, and their derivatives such as genistein and daidzein (e.g., such as soy and clover extracts, extracts containing resveratrol and the like. Examples of such natural extracts include grape seed, green tea, pine bark, and propolis.

Progesterones, and naturally-derived ingredients with progesterone-like activity, on the other hand, may be useful, as well as astringents such as witch hazel, triclosan, cerulenin, alpha-methylene-gamma-butyralactone, glycine derivatives such as capryloylglycine and methylglycine, salicylic acid, or benzoyl peroxide.

Fabao 101, which has the following active ingredients, may also be included in the compositions of this invention: *Aralia Quinquetolia, Astragalus Glycyphyllos, Angelica Arhangelica* Root, *Salvia Officinalis, Capsicum, Carya Alba, Corthamis Tinctorius*, Cortex dictamni radicis, Flos Chrysanthemum, Heshouwu, Iron-Fist Ginseng, Miltiorrhizae, *Notoginseng*, Paorulca Glandulosa, Peach Kernel Oil, Rhizome of Szechuan Lovage, Radix astragali, Radix Ginseng, Radix Polygoni Multiflori, Red-rooted Salvia, Rhizhoma gastroidia ginseng, Seu radix notopterygii, *Sophera flavescens*.

Other Materials

Various other materials may also be present in the compositions useful in the subject invention. These include humectants, proteins and polypeptides, preservatives and an alkaline agent. Examples of such agents are disclosed in the INCI Handbook, pp. 1650-1667. The compositions of the present invention may also comprise chelating agents (e.g., EDTA) and preservatives (e.g., parabens). Examples of suitable preservatives and chelating agents are listed in pp. 1626 and 1654-55 of the INCI Handbook. In addition, the topical compositions useful herein can contain conventional cosmetic adjuvants, such as dyes, opacifiers (e.g., titanium dioxide), pigments, and fragrances.

Darkening Agents

In one embodiment, the compositions of the present invention further contain darkening agents such as melanin or synthetic melanin derivatives, or melanin-like molecules, vanillin polymers, natural extracts such as, but not limited to Coleus Forskoli extract, Bugrane-P extract, extracts from natural sources containing pigments (e.g., brown pigments from plants from the *Hedychium* genus or *Bearberry* genus or yellow, orange and red pigments, from plants containing carotenoids or canthaxanthins); or synthetic chemicals such as compounds containing copper (e.g., copper salts such as $CuCl_2$) or synthetic carotenoids or canthaxantins. Examples of synthetic melanin derivatives are set forth in U.S. Pat. Nos. 5,618,519, 5,384,116, and 5,227,459. Examples of soluble melanin derivatives are set forth in 5,744,125, 5,225,435, 5,218,079, and 5,216,116. Examples of commercially available soluble melanin derivatives include Melasyn-100™ from San-mar laboratories, Inc. (Elmsford, N.Y.) and MelanZe™ from Zylepsis (Ashford, Kent, United Kingdom).

These agents will preferably be present in the composition in an amount from about 0.001% to about 10% by weight, in particular in an amount from about 0.01% to about 5% by weight.

In another embodiment, the composition may include a peptide. Examples of darkening peptides are set forth in U.S. Pat. No. 7,025,951. The peptide of the invention set forth therein may be provided in the form of cosmetically acceptable salts. Examples of preferred salts are those with therapeutically acceptable organic acids, e.g., acetic, palmitic, oleic, stearic, lactic, maleic, citric, malic, ascorbic, succinic, benzoic, salicylic, methanesulfonic, or Palmoic acid, as well as polymeric acids such as tannic acid or carboxymethyl cellulose, and salts with inorganic acids such as the hydrohalic acids (e.g., hydrochloric acid), sulfuric acid or phosphoric acid.

The amount of peptide present in the composition depends on the peptide used. The peptide should be present in the composition in an amount from about 0.001% to about 10% by weight, in particular in an amount from about 0.005% to about 5% by weight.

Mineral Water

The compositions of the present invention may be prepared using a mineral water, for example mineral water that has been naturally mineralized such as Evian® Mineral Water (Evian, France). In one embodiment, the mineral water has a mineralization of at least about 200 mg/L (e.g., from about 300 mg/L to about 1000 mg/L). In one embodiment, the mineral water comprises at least about 10 mg/L of calcium and/or at least about 5 mg/L of magnesium.

Methods of Use

The compositions of this invention may be utilized to induce hair growth by topical application of said compositions to the area of the body on which hair growth is desired. Preferably, the compositions of this invention are applied topically to the desired area of the body at least once per day for at least three weeks but preferably on a daily for at least fourteen weeks and more preferably, indefinitely. For improvement to hair quality, said compositions should be applied at least once per day for at least six weeks. After six weeks, the user should observe increased hair growth and should be able to observe increased hair shaft diameter and/or enhanced visual attributes of the hair, such as hair volume, hair shine and hair thickness.

Example 1

Extract Preparation

The following is a description of the preparation of the extract of this invention. As used in the subsequent Examples, the weight percentage of extract refers to the weight of the liquid extract.

*Cotinus coggygria* leaves (whole dried leaves including sticks) were purchased from Bulgarcoop Ltd/Bilkocoop (Sofia, Bulgaria), Bilec (Troyan, Bulgaria), and Harbin Medicines & Health Products IMP. & EXO. Co., LTD. (Harbin, China) and Monteagle Herbs (Canada) Killaloe, ON.

One hundred grams of whole herb leaves were crushed, larger sticks removed and crushed leaves were placed in 1 liter (L) of boiling water and boiled for five (and up to thirty) minutes in a sealed container with agitation as needed. After the boiling process was complete, the container was immediately withdrawn from the heating source, kept covered, and stored at room temperature for from about 1 hour to about 12 hours. This may be accompanied with occasional agitation; the longer the mixture is stored, the less agitation may be needed. The extract was then filtered through gauze, and excess liquid was squeezed manually from herbs to maximize the extract yield. This constitutes a *Cotinus coggygria* extract of about 30 mg/ml as determined using an HR73 Moisture Analyzer (Mettler-Toledo, Inc., Columbus, Ohio).

Different concentrations of the *Cotinus coggygria* extract were prepared. The extract was further concentrated by respectively reducing the volume to 2, 5 and 7 times its original yield producing a 60 mg/ml, 150 mg/ml and 210 mg/ml extracts. This process was achieved by heating and evaporation on a stirrer plate between 80° C.-85° C. The extract was then refrigerated and could be stored at 4° C. without losing activity.

*Cotinus* extract formulations were prepared as follows, containing quantities as listed according to the table below (ml units): Either deionized water or 60 mg/ml (2×), 90 mg/ml (3×), 120 mg/ml (4×), 150 mg/ml (5×) and 210 mg/ml (7×) *Cotinus coggygria* extracts were added to a mixing vessel and agitation initiated at room temperature. Then, $Na_2EDTA$ was added and mixed until dissolved. Following this process, glycerin was added and mixing continued until the mixture was uniform. Once uniformity was achieved, dimethicone and a preservative were added and mixing was continued (note that these ingredients will not go into solution). While this process continued, the dimethyl isosorbide ("DMIS") and BHT were premixed until clear and uniform. The DMIS/BHT premixture was then added to the batch. Finally, the Laureth-7 & C13-14 Isoparaffin was added mixing and agitation continued until a completely homogenous substance was achieved. Mixing speed was adjusted during the process to facilitate the batch to thicken and maintain content uniformity.

Alternatively, 150 mg/ml *Cotinus coggygria* extract was prepared via the process of lyophilization as follows: 30 mg/ml *Cotinus* extract was prepared as described above and lyophilized in a Genesis freeze dryer from VirTis (Gardiner, N.Y.). A standard freeze-drying cycle includes a freezing temperature of −70 C.° and drying vacuum of 20 mmHg. This cycle may be repeated to remove all the water from the extract. Solid weight was determined by weighing the container before and after lyophilizing, and deionized water was added to dissolve the solid into 150 mg/ml *Cotinus*. Alternatively, the preparation can be diluted further with deionized water to lower concentrations down to 60 mg/ml *Cotinus*. These extracts were then frozen at −20 C.° for long-term storage.

In addition to the formulation prototype described above, a 150 mg/ml (5×), formulations were prepared based on the above descriptions with the following adjustments:
 i) DMIS was excluded from the formulation (referred to as 150 mg/ml w/o DMIS)
 ii) Sepigel 305 was substituted with SepiPlus400 iii) Lyophilized Cotinus extract was used with the formulation prototypes described above, or in a vehicle consisting of 70% ethanol and 30% propylene glycol.

TABLE I

Formulations containing *Cotinus coggygria*

| INCI Name | Control (%) Placebo | *Cotinus* (%) 1× extract | 2× extract | 5× extract |
|---|---|---|---|---|
| Water | 87.20 | | 0 | |
| *Cotinus coggygria* extracts | 0.00 | 85.7 | 85.3 | 84.7 |
| Phenoxyethanol & Methylparaben & Propylparaben & Ethylparaben[1] | 1.00 | | 1.00 | |
| Disodium EDTA[2] | 0.05 | | 0.05 | |
| Dimethicone[3] | 2.00 | | 2.00 | |
| Glycerin | 1.50 | | 1.50 | |
| Polyacrylamide & Laureth 7 & C13-14 Isoparrafin[4] | 3.20 | 4.7 | 5.1 | 5.7 |
| BHT | 0.05 | | 0.05 | |
| Dimethyl Isosorbide[5] | 5.00 | | 5.00 | |
| Total | 100.00 | | 100.00 | |

[1] Available as "Phenonip XB" from Clariant Corporation of Mount Holly, NC.
[2] Available as "Versene NA" from the Dow Chemical Company of Midland, Michigan.
[3] Available as "DC 200 Fluid 100 cs." From Dow Corning of Midland, Michigan.
[4] Available as "Sepigel 305" from Seppic of Montanoir, Paris, France.
[5] Available as "Arlasolve DMI" from Uniquema of New Castle, Delaware.

Example 2

Lyophilization of *Cotinus coggygria* Extract/Extract Concentration

Different concentrations of the *Cotinus coggygria* extract may be prepared by the process of lyophilization. The 30 mg/ml *Cotinus* extract may be lyophilized in a Genesis freeze dryer from VirTis (Gardiner, N.Y.). A standard freeze drying cycle includes a freezing temperature of −70 C.° and drying vacuum of 20 mmHg. This cycle may be repeated to remove all the water from the extract. Solid weight may then be determined by weighing the container before and after lyophilizing. Deionized water may then be added to dissolve the solid into e.g. 150 mg/ml or 210 mg/ml *Cotinus*), or dilute further to e.g. 60 mg/ml Cotinus). These extracts may then be frozen at −20 C.° for long-term storage.

Example 3

Hair Growth Induction in C3H Mice by *Cotinus coggygria* Extract

C3H female mice age 6-7 weeks of age were purchased from Taconic Farms (Germantown, N.Y.). Mice were housed in appropriately sized cages in an environmentally controlled room with a 12-hour light-12-hour dark photoperiod and supplied with food and water ad libitum. Animal care was based on the "Guide for the Care and Use of Laboratory Animals", NIH Publication No. 85-23. Animals were acclimated for a week before study starts. Once all mice entered their prolonged telogen/resting phase (about 50-60 days long) of the hair cycle, they were clipped over the dorsal area about 1.5×5 cm (Wahl Clippers 8900 Series, Blade # 1086). Seven female mice per group were clipped while sedated with 2% induction and maintenance isoflurane and 0.5 L Oxygen. In addition to the 150 mg/ml *Cotinus coggygria* formulation, the treatment groups included a placebo, 5% Minoxidil as positive control and an untreated group to serve as control for natural hair growth initiation and to observe placebo effects. 200 μl of test materials were applied topically to the area daily, 5 days a week. Images were taken at the first signs of anagen/active growth phase and when needed based on visual observation. Skin samples were obtained for histological analysis at week 3 and a study log documenting day-to-day observations of mice entering anagen (grey skin, the first visual clue to a new hair growth) were recorded. Treatments continued for up to 6 weeks. Surprisingly, the 150 mg/ml *Cotinus* composition induced hair growth in the C3H mice faster than 5% Minoxidil.

TABLE II

Hair growth induction in C3H mice representing % of mice entering anagen as a function of time (days of study)

| Groups | Day | | | | | | | | | | | | | | | |
|---|---|---|---|---|---|---|---|---|---|---|---|---|---|---|---|---|
| | 9 | 10 | 13 | 14 | 16 | 20 | 22 | 23 | 24 | 27 | 29 | 31 | 35 | 42 | 43 | 44 |
| Placebo | 0 | 0 | 0 | 0 | 0 | 0 | 0 | 0 | 0 | 0 | 0 | 0 | 0 | 0 | 0 | 0 |
| Best 5% Minoxidil | 20 | 40 | 40 | 80 | 80 | 80 | 80 | 80 | 75 | 75 | 100 | 100 | 100 | 100 | 100 | 100 |
| Ave 5% Minoxidil N = 4 | 7 | 18 | 18 | 31 | 31 | 32 | 41 | 38 | 36 | 36 | 36 | 45 | 48 | 63 | 87 | 93 |
| 150 mg/ml | | | | | | | | | | | | | | | | |

TABLE II-continued

Hair growth induction in C3H mice representing % of mice entering anagen as a function of time (days of study)

| | Day | | | | | | | | | | | | | | | |
|---|---|---|---|---|---|---|---|---|---|---|---|---|---|---|---|---|
| Groups | 9 | 10 | 13 | 14 | 16 | 20 | 22 | 23 | 24 | 27 | 29 | 31 | 35 | 42 | 43 | 44 |
| Cotinus | 0 | 57 | 71 | 86 | 100 | 100 | 100 | 100 | 100 | 100 | 100 | 100 | 100 | 100 | 100 | 100 |
| Untreated | 0 | 0 | 0 | 0 | 0 | 0 | 0 | 0 | 0 | 0 | 0 | 0 | 0 | 0 | 0 | 0 |

Number per group: Day 9-22 (N = 7), Day 23-26 (N = 6), Day 27-44 (N = 5)

Example 4

Hair Quality Improvement in C3H Mice by *Cotinus coggygria* Extract

C3H female mice age 6-7 weeks of age were purchased from Taconic Farms (Germantown, N.Y.), and treated as described in Example 3. Hair samples were obtained in the telogen/resting phase of all animals at week 14 of treatments by plucking hair from sacrificed mice, several club hairs were selected from the placebo and the 150 mg/ml *Cotinus* treated groups, and were analyzed by Scanning Electron Microscopy (SEM) and visual microscopy (×400). Surprisingly, the 150 mg/ml *Cotinus* composition resulted in thicker hair shaft diameter and in smoother hair cuticles in the C3H mice, as compared to placebo treated hairs.

Example 5

Hair Growth Induction by Different Concentrations of *Cotinus coggygria* Extract C3H mice were treated as described in Example 3. In addition to the 150 mg/ml *Cotinus coggygria* formulation prepared as a concentrate via heat processing, a lyophilized *Cotinus* extract powder was prepared as described above, as well as lower (60 mg/ml, 90 mg/ml, 120 mg/ml) and higher concentrations (up to 210 mg/ml) of *Cotinus coggygria* extracts (Table III). The treatment groups included a placebo, 5% minoxidil as positive control and an untreated group to serve as control for natural hair growth initiation and to observe placebo effects. 200 ul of test materials were applied topically to the area daily, 5 days a week. Images were taken at the first signs of anagen/active growth phase and when needed based on visual observation. Skin samples were obtained for histological analysis and a study log documenting day-to-day observations of mice entering anagen (grey skin) were recorded. Treatments continued for up to 6 weeks. Results of this study are shown in Table III. These results show that the 150 mg/ml *Cotinus* Lyophilized extract induced anagen equally well as the heat-processed 150 mg/ml *Cotinus* extract. Moreover, a dose-dependent increase in dorsal hair coverage was observed visually and documented by images, and also confirmed by histological analysis. The 60 mg/ml dose was the lowest dose inducing hair growth in the C3H model with the 150 mg/ml concentration being the most efficient dose inducing hair growth with the formulation prototype containing DMIS. The 210 mg/ml induced hair growth similar to the formulation containing no DMIS resulting in anagen entry two days earlier, and resulted in accelerated follicular cycling inducing a second anagen phase.

The 120 mg/ml induced hair growth in the C3H mice similar to 5% Minoxidil, whereas the higher concentrations induced hair growth faster than 5% Minoxidil.

Example 6

*Cotinus coggygria* Extracts Synergize with Minoxidil

C3H female mice clipped over the dorsal area once they have entered their prolonged telogen phase (about 8 weeks long) were topically treated once daily for 6 weeks with 200 µl 150 mg/ml of *Cotinus coggygria* extract or with 5% Minoxidil or with the combination of both agents. Visual observations revealed that topical treatment with 150 mg/ml *Cotinus* extract in combination with 5% Minoxidil resulted in improved dorsal coverage as compared to each agent alone. Although initial anagen induction visually occurred at a similar time in both the 150 mg/ml *Cotinus* and 150 mg/ml *Cotinus*+5% Minoxidil groups, full dorsal coverage was achieved with the combination at an earlier time than with the individually treated agents (see Table III). Histological analysis (F&M staining) of day 8 dorsal skin sections of topically treated C3H mice revealed denser hair follicles per field of vision when combining the *Cotinus* extract with the benchmark 5% Minoxidil compared to *Cotinus* and Minoxidil treatments alone.

Example 7

Hair Growth Induction in C57BL/6 Mice by *Cotinus coggygria* Extract

C57BL/6 mice of age 6-8 weeks of age were purchased from Taconic Farms (Germantown, N.Y.). Mice were housed in appropriately sized cages in an environmentally controlled room with a 12-hour light-12-hour dark photoperiod and supplied with food and water ad libitum. Animal care was based on the "Guide for the Care and Use of Laboratory Animals", NIH Publication No. 85-23. Animals were acclimated for a week before study starts. Mice in the telogen phase of the hair cycle were clipped over the dorsal area about 1.5×5 cm. 200 µl of test materials (as described in Table I) were applied topically to the area daily, 5 days a week. In addition to the 150 mg/ml *Cotinus coggygria* formulation, the treatment groups included a placebo and 60 mg/ml *Cotinus coggygria* formulation. By week two all the mice in the 150 mg/ml *Cotinus* group (N=4) had entered the anagen phase and started growing hair in the upper dorsal area whereas no signs of anagen or hair growth were present in the placebo or 60 mg/ml *Cotinus* groups. This example shows that the hair induction properties of the *Cotinus* extract are not related to properties of the C3H mouse strain.

Example 8

Effect of Formulation Components on Hair Re-Growth with *Cotinus coggygria*

C3H hair growth studies were performed as described in earlier examples, with the addition of formulation agents to the *cotinus* extract preparation. Surprisingly, the addition of 5% DMIS and Sepiplus 400 (electrolyte tolerant thickening polymer) to the 150 mg/ml *Cotinus* extract resulted in a delayed entry into anagen than that of the 150 mg/ml extract alone, or containing Sepiplus 305 without DMIS (see Table II for results). Histological analysis (F&M staining at day 8 and day 11) of C3H mice topically treated with 150 mg/ml *Cotinus* extract formulated respectively with and without 5% DMIS revealed that when DMIS was omitted from the formulation that there was a more expedited entry into anagen. This example suggests that formulations of *Cotinus* extract for hair growth products should not use all known formulation agents known to the skilled in the art, but should be selected based on an efficacy test.

extracts. The mice were sacrificed by $CO_2$ inhalation 5.5 hours after the TPA treatment, the left and right ears were removed and a 7 mm biopsy was removed from each ear and weighed. The difference in biopsy weights between the right and left ear was calculated. Anti-inflammatory effects of compounds are demonstrated by the inhibition of the increase in ear weight.

*Cotinus* formulations with 30 mg/ml and 60 mg/ml extract concentration showed a dose-dependent inhibition of TPA-induced mouse ear edema. Surprisingly, the 150 mg/ml *Cotinus* formulation did not show the inhibitory activity and the effect was not different from the placebo. This experiment indicates that the 150 mg/ml *Cotinus* extract is physically different from other *Cotinus* extracts.

TABLE IV

Anti-inflammatory effects of *Cotinus* formulations

| Test Material | Inflammation (Edema, mg) | % Inhibition* |
|---|---|---|
| Placebo | 8.26 ± 0.69 | — |
| 30 mg/ml *Cotinus* | 4.50 ± 0.73** | 45.7% |

TABLE III

Hair growth induction in C3H mice representing % of mice entering anagen as a function of time (days of study)

| Groups | Day | | | | | | | | | | | | | | | |
|---|---|---|---|---|---|---|---|---|---|---|---|---|---|---|---|---|
| | 8 | 9 | 10 | 11 | 14 | 15 | 16 | 17 | 18 | 21 | 22 | 23 | 24 | 25 | 28 | 29 |
| 5% Minoxidil | 0 | 0 | 14 | 43 | 33 | 33 | 33 | 20 | 40 | 80 | 80 | 80 | 80 | 80 | 80 | 80 |
| 60 mg/ml *Cotinus* | 0 | 0 | 0 | 0 | 0 | 0 | 0 | 0 | 0 | 0 | 0 | 0 | 0 | 0 | 20 | 20 |
| 90 mg/ml *Cotinus* | 0 | 0 | 0 | 0 | 0 | 0 | 17 | 0 | 0 | 0 | 20 | 20 | 20 | 20 | 40 | 80 |
| 120 mg/ml *Cotinus* | 0 | 0 | 14 | 14 | 0 | 0 | 17 | 60 | 80 | 100 | 100 | 100 | 100 | 100 | 100 | 100 |
| 150 mg/ml *Cotinus* | 0 | 57 | 71 | 86 | 83 | 83 | 83 | 100 | 100 | 100 | 100 | 100 | 100 | 100 | 100 | 100 |
| 150 mg/ml *Cotinus* Lyophilized | 0 | 57 | 71 | 100 | 100 | 100 | 100 | 100 | 100 | 100 | 100 | 100 | 100 | 100 | 100 | 100 |
| 150 mg/ml *Cotinus* + Sepiplus400 | 0 | 14 | 14 | 14 | 0 | 0 | 33 | 40 | 80 | 100 | 100 | 100 | 100 | 100 | 100 | 100 |
| 150 mg/ml *Cotinus* + 5% Minoxidil | 0 | 43 | 86 | 86 | 83 | 83 | 100 | 100 | 100 | 100 | 100 | 100 | 100 | 100 | 100 | 100 |
| 150 mg/ml *Cotinus* w/o DMIS | 50 | 100 | 100 | 100 | 100 | 100 | 100 | 100 | 100 | 100 | 100 | 100 | 100 | 100 | 100 | 100 |
| 210 mg/ml *Cotinus* | 37 | 100 | 100 | 100 | 100 | 100 | 100 | 100 | 100 | 100 | 100 | 100 | 100 | 100 | 100 | 100 |
| Placebo with DMIS | 0 | 0 | 0 | 0 | 0 | 0 | 0 | 0 | 0 | 0 | 0 | 0 | 0 | 0 | 0 | 0 |
| Placebo w/o DMIS | 0 | 0 | 0 | 0 | 0 | 0 | 0 | 0 | 0 | 0 | 0 | 0 | 0 | 0 | 0 | 0 |
| Untreated | 0 | 0 | 0 | 0 | 0 | 0 | 0 | 0 | 0 | 0 | 0 | 0 | 0 | 0 | 0 | 0 |

Number per group: Day 0-8 (N = 8), Day 9-11 (N = 7), Day 17-(N = 5)
Note:
All *Cotinus* formulations contain DMIS unless otherwise indicated

Example 9

*Cotinus coggygria* Formulations of Low Concentrations Inhibit TPA-Induced Mouse Ear Edema The following experiments were carried out to test the effect of Cotinus formulations (see Table I) in a phorbol ester (TPA) induced edema assay using the method of Rao et al (Rao T S, Currie J L, Shaffer A F, Isakson P C. Comparative evaluation of arachidonic acid (AA)- and tetradecanoylphorbol acetate (TPA)-induced dermal inflammation. *Inflammation* 1993; 17: 723-741). Albino male CD-1 mice, 7-9 weeks old, were housed as described in earlier examples. A 0.005% (w/v) TPA solution was made in acetone. A 20 μL volume of this TPA solution was applied to the dorsal left and right ears of the mouse. *Cotinus* extracts formulated as described in Table III were applied to the left ear (20 μL) immediately after TPA application. The right ear was not treated with these TABLE IV-continued Anti-inflammatory effects of *Cotinus* formulations

| Test Material | Inflammation (Edema, mg) | % Inhibition* |
|---|---|---|
| 60 mg/ml *Cotinus* | 3.38 ± 1.20** | 59.25% |
| 150 mg/ml *Cotinus* | 9.28 ± 1.49 | −11.98% |

*% Inhibition = (Vehicle treated biopsy weight − Agent(s) treated biopsy weight)/(Vehicle treated biopsy weight) × 100
**Indicates significant difference from Placebo using a student's t-Test with significance set at P < 0.05.

What is claimed is:
1. A method of enhancing hair growth by applying to the scalp of a patient a topically active composition comprising a concentration of at least 90 mg/ml of a *Cotinus coggygria* extract, which increases hair coverage to the scalp after daily application for at least three weeks.

2. A method of enhancing hair quality by applying to the scalp of a patient a topically active composition comprising a concentration of at least 90 mg/ml of a *Cotinus coggygria* extract, which increases hair shaft diameter and results in smoother and shinier hair cuticles after daily application for at least six weeks increased hair shaft diameter and smoother and shinier hair cuticles.

* * * * *